(12) United States Patent
Brenneis et al.

(10) Patent No.: US 8,758,708 B2
(45) Date of Patent: Jun. 24, 2014

(54) DEVICE FOR COLLECTING LIQUID SAMPLES FOR A VAT

(75) Inventors: Christophe Brenneis, Saint Victor la Coste (FR); Hervé Lagrave, Tresques (FR); Jacques Mamert, Saint Germain les Corbeil (FR)

(73) Assignee: Commissariat a l'Energie Atomique et aux Enegies Alternatives, Paris (FR)

( * ) Notice: Subject to any disclaimer, the term of this patent is extended or adjusted under 35 U.S.C. 154(b) by 0 days.

(21) Appl. No.: 13/497,647

(22) PCT Filed: Sep. 24, 2010

(86) PCT No.: PCT/EP2010/064161
§ 371 (c)(1),
(2), (4) Date: Jun. 6, 2012

(87) PCT Pub. No.: WO2011/036257
PCT Pub. Date: Mar. 31, 2011

(65) Prior Publication Data
US 2012/0321535 A1    Dec. 20, 2012

(30) Foreign Application Priority Data
Sep. 25, 2009    (FR) .................................. 09 56644

(51) Int. Cl.
*B01L 3/02* (2006.01)
*G01N 1/00* (2006.01)
*G01N 1/14* (2006.01)
*G01N 33/00* (2006.01)
*G01N 1/10* (2006.01)

(52) U.S. Cl.
CPC .......... *G01N 1/14* (2013.01); *G01N 2033/0093* (2013.01); *G01N 2001/1037* (2013.01); *G01N 2001/1463* (2013.01)
USPC ........... 422/521; 422/512; 422/522; 422/537; 422/538; 141/309

(58) Field of Classification Search
USPC ................. 422/501, 509, 512, 515, 521–522, 422/537–538; 73/863.83, 864.15; 141/267, 141/309, 325, 329
See application file for complete search history.

(56) References Cited

U.S. PATENT DOCUMENTS

| 4,450,730 A | 5/1984 | Levos et al. |
| 4,638,675 A * | 1/1987 | Sperinck et al. ........... 73/864.34 |
| 4,674,343 A | 6/1987 | Larson |

(Continued)

FOREIGN PATENT DOCUMENTS

| EP | 0063971 A1 | 11/1982 |
| EP | 0155107 A2 | 9/1985 |
| EP | 0296917 A1 | 12/1988 |

OTHER PUBLICATIONS

International Search Report for PCT/EP2010/064161; Jan. 19, 2011.

*Primary Examiner* — Brian R Gordon
(74) *Attorney, Agent, or Firm* — Pearne & Gordon LLP (57) ABSTRACT

It comprises, in addition to a sampling system (3), at the outlet of a vat (1) containing the liquid to be sampled, a selector (4) that establishes switching on an array of similar vats (1), and especially a suction unit (5) that operates by releasing compressed air into a nozzle (28); the airflow direction is controlled by a valve (29) between a direction directed toward the outlet (6), causing the suction of the liquid from the vat (1), and an opposite direction when the valve (29) is closed, feeding the liquid back into the vat (1) and cleaning the pipe (2).

9 Claims, 4 Drawing Sheets

(56) References Cited

U.S. PATENT DOCUMENTS

| | | | |
|---|---|---|---|
| 5,310,683 A * | 5/1994 | Godec et al. | 436/123 |
| 5,353,652 A | 10/1994 | Houck | |
| 5,417,105 A * | 5/1995 | Martinez et al. | 73/40.7 |
| 5,837,203 A * | 11/1998 | Godec et al. | 422/509 |
| 5,976,468 A * | 11/1999 | Godec et al. | 422/501 |
| 6,271,043 B1 * | 8/2001 | Godec et al. | 436/180 |
| 6,524,531 B1 * | 2/2003 | Feygin | 422/522 |
| 8,003,048 B2 * | 8/2011 | Clay et al. | 422/63 |

\* cited by examiner

DEVICE FOR COLLECTING LIQUID SAMPLES FOR A VAT

FIELD OF THE INVENTION

The invention relates to a device for collecting liquid samples from a vat, and even from a plurality of vats.

BACKGROUND OF THE INVENTION

Such devices are common in the nuclear industry in order to analyse certain liquids loaded with irradiating materials. The corresponding devices are generally placed in shielded units, and they are manipulated through the use of remote manipulators. The liquid to be analysed is first present in a vat. It undergoes a suction through a pipe exiting into the top of the vat, which carries it toward a sampling holder whereon a small container, generally called a jug, has been installed, and it partially fills this jug. The excess liquid is evacuated toward an outlet or returns to the vat by flowing through the pipe, which is inclined, as soon as the suction has stopped.

A disadvantage with these devices is that the return to the vat is not complete and that droplets of liquid remain on the pipe, and then crystallise: this can be considered as a pollutant, and limits the quality of the following measurements by mixing with the samples sucked thereafter when the original liquid of the vat has been replaced with another. Another disadvantage with these devices is that it is difficult to join them to an array of vats in order to sample by choice samples from any one of them.

The invention has for object to eliminate these disadvantages, and above all to allow for a sufficient cleaning of the pipe and of the pipes leading to the vats without substantially complicating the device or having it lose its faculty to be able to be actuated via remote handling.

BRIEF SUMMARY OF THE INVENTION

In a general form, it relates to a device for collecting liquid samples from at least one vat, comprising at least one pipe connecting to a respective vat and ending at an outlet at an end opposite the vat, a sampling jug holder of samples arranged on the pipe, and a suction unit of the contents of the vat in the pipe, characterised in that the suction unit comprises a nozzle arranged on the pipe, a compressed air inlet exiting in the nozzle, and the device further comprises a valve for sealing off the pipe, arranged on the pipe between the nozzle and the outlet.

This arrangement makes it possible to use compressed air to produce the suction by releasing pressure in the nozzle, then, as soon as the valve is closed, to clean the pipe by reversing its circulation toward the vat, which rejects the droplets of the liquid that are still contained therein.

The pipe advantageously comprises a small reservoir and the sampling jug holder is able to be connected to the small reservoir by the intermediary of a self-sealing quick-coupling in two portions, a first of said portions belonging to the small reservoir and a second of said portions comprising a needle which penetrates inside the small reservoir by passing through the first portion: this arrangement makes it possible to have a jug holder that can be manipulated easily via a remote manipulator in order to be installed on the device for collecting, then withdrawn to remove the jug and replace it without difficulty away from the device.

The pipe is advantageously wider on the side of the nozzle which leads from the outlet than toward the opposite side, which leads toward the vat. This device facilitates the proper direction of the compressed air when it arrives at the nozzle, toward the outlet when the valve is open, thanks to the lower resistance that it encounters from this side.

In order to facilitate the maintenance of the device although only remote manipulations are possible, it is recommended that the nozzle and the valve form a single and removable unit with a portion of the pipe and a portion of the compressed air inlet, said portions being connected to main portions of the pipe and of the compressed air inlet by capstan connectors.

According to a perfected embodiment, the device comprises a plurality of vats and pipes, the pipes connecting in turn to a selector, and then comprising a joint portion toward the outlet, whereon the nozzle and the valve are arranged.

The device can then serve several vats and several pipes. A favourable embodiment comprises a rotating selector which comprises a cylindrical mobile element provided with an external member for manoeuvring, the mobile element comprising an axial piercing directed toward the outlet and a radial piercing directed toward the vats and connections of the pipes arranged on a portion of a turn of the selector.

The invention shall now be described more completely and for the purposes of illustration in liaison with the figures.

BRIEF DESCRIPTION OF THE SEVERAL VIEWS OF THE DRAWINGS

FIG. 2 is a general view of the sampling (2A as a unit, 2B as an exploded view)

DETAILED DESCRIPTION OF THE INVENTION

Figure 1:
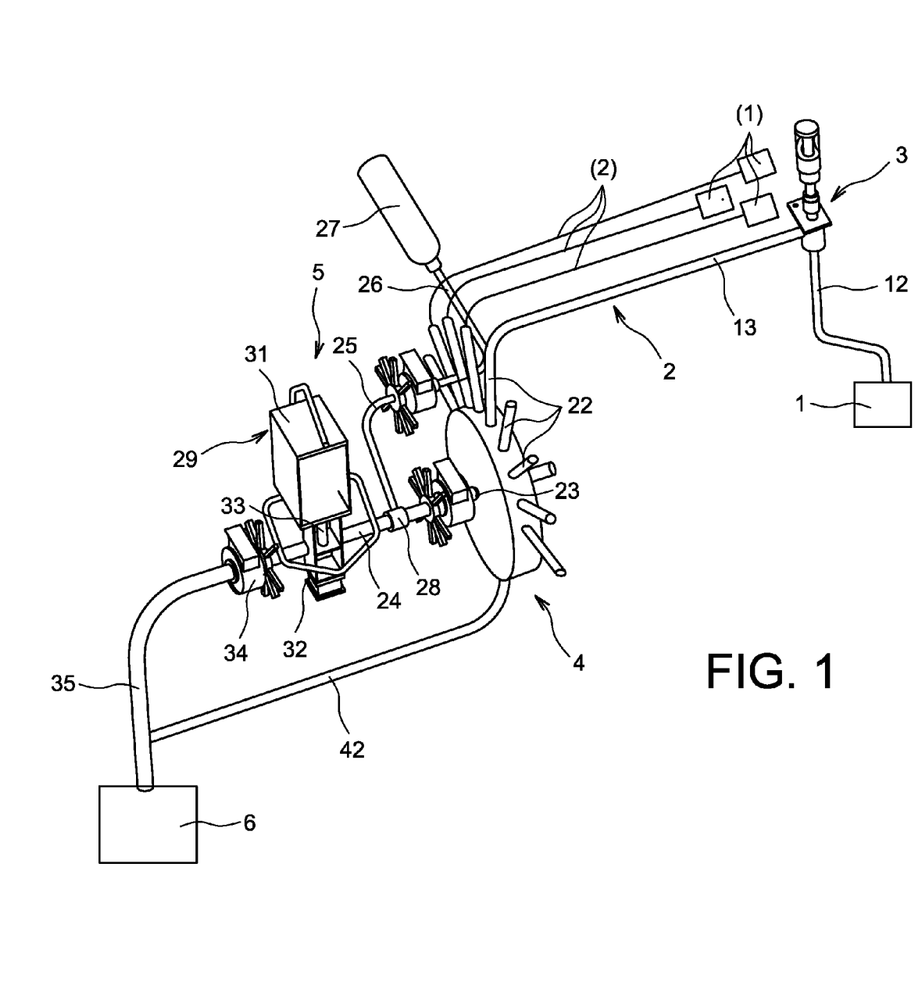
FIG. 1 is a general view of the invention.

Reference shall first be made to FIG. 1. The liquid to be sampled is initially located in storage vats 1. Pipes 2 for sampling exit at the top of the vats 1, pass through a sampling installation 3, respective, are connected to a joint selector 4, then pass through a suction unit 5, and finish toward an outlet 6 which is a reservoir for collecting the excess sucked liquid. The main elements of the device shall now be described successively. The pipes 2 rise first from the vats 1, to the sampling installations 3, then fall little by little toward the outlet 6, opposite the vats 1 and therefore separate from them.

Figure 2A:
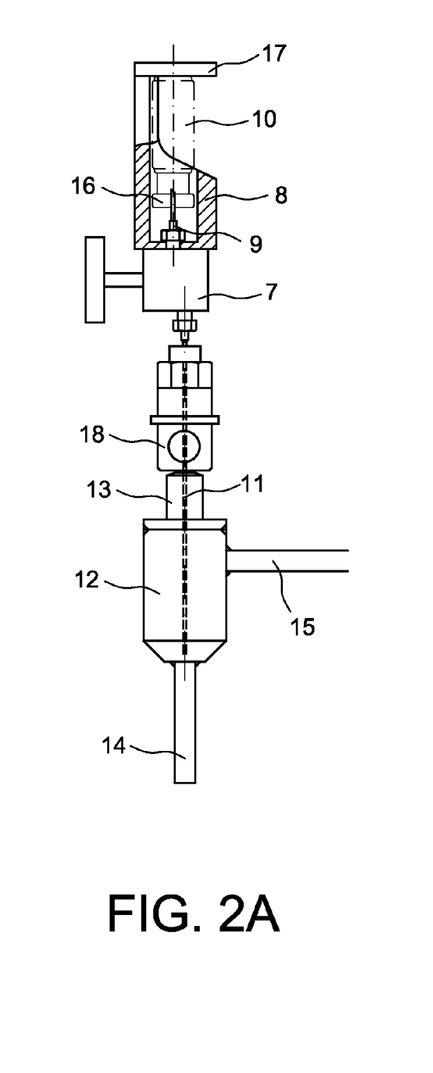
Figure 2B:
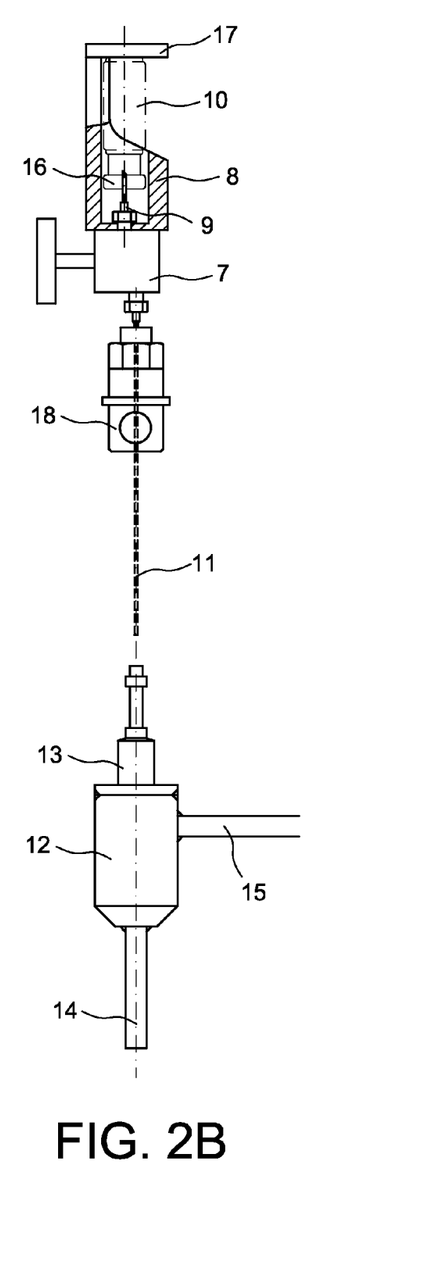

The sampling system 3 is shown in detail in FIG. 2. It first comprises a mobile portion constituted of a manual valve 7 of which the top is occupied by a cylindrical case 8 open at the top comprising an upper needle 9 whereon can be installed the jug 10 and a pivoting portion 17 making it possible to imprison the jug 10 in its housing, and the base via a needle 11 whereon is fixed a female self-sealing quick-coupling 18 and through which the sampling will be carried out. In the case of a plurality of vats to be sampled, this mobile portion is displaced and is provided with a new jug.

The unit further comprises a fixed portion comprising a small reservoir 12 closed by a male self-sealing quick-coupling 13 and wherein exit a lower surface 14 of the pipe 2 leading to the vat 1, a second surface 15 of the pipe 2 leading to the selector 4. In order to take a sample, the mobile portion is installed on the fixed portion, through the insertion of the needle 11 in the coupling 13 to connexion of the female quick-coupling 18 on the male quick-coupling 13. A new jug 10 was installed beforehand in the mobile portion on the needle 9, the manual valve 7 being in closed position. These jugs are hermetic and the vacuum therein is created at the onset. Their septum 16 is made of rubber and can be pierced by the needle 9 when the jugs 10 are pressed onto it. This is done when a suction has made it possible to fill the small reservoir 12 with the liquid to be sampled: the manual valve 7 is open and the vacuum present in the jug 10 then sucks a portion of the liquid via the needle 11, the manual valve 7 and the needle 9. After which, the manual valve 7 can be closed, and the mobile portion can be withdrawn through disconnection of the quick-couplings 13 and 18. The jug 10 can be withdrawn, and the piercing made in the septum 16 closes itself.

Figure 3:
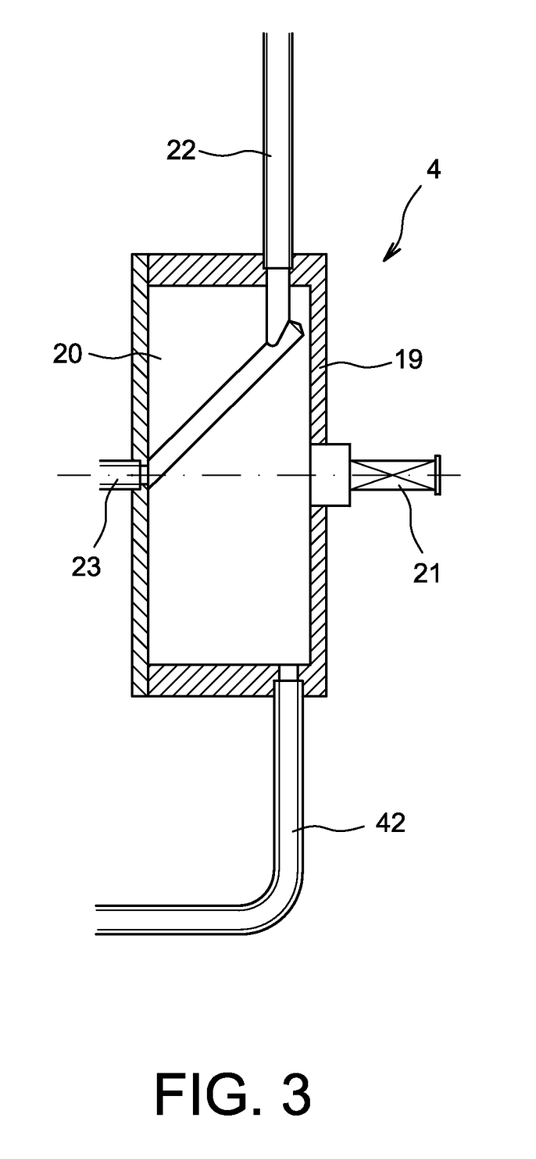
FIG. 3 is a view of the selector,
FIG. 4 a view of the nozzle and
FIG. 5 a view of the capstan connector.

Reference is again made to FIG. 1, and to FIG. 3, for the description of the selector 4. It comprises a casing 19 occupied by a cylindrical plug 20, provided with a member for manoeuvring in the form of a square shaft tip 21 protruding out of the casing 19. To the casing 19 is connected connectors 22 extending the second surfaces 13 of the pipes 2 and which extend in a radiating direction from the casing 19 over a portion of the turn. Another connector 23 is connected to the casing 19, but this time in the axial direction, opposite the square shaft tip 21. This connector 23 is connected to the suction unit 5. The plug 20 contains a piercing 43 leading to the connector 23 by an axial portion and, according to the rotation of the square shaft tip 21, to one or the other of the connectors 22 via a radial portion. The selector 4 makes it possible to select the vat 1 from which the liquid is sampled, according to its manoeuvre and by means of the arrangements described now.

Figure 4:
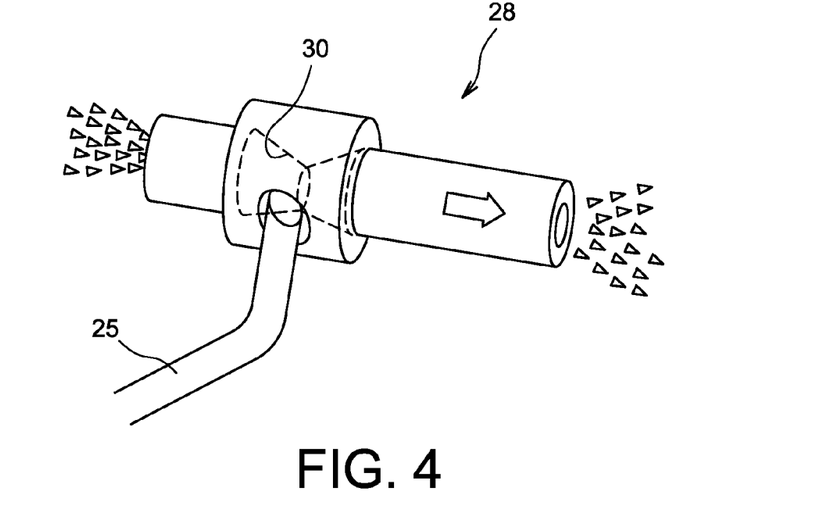

The suction unit 5 comprises a removable portion of the pipe 2, a removable portion 25 of a compressed air inlet 26 connected to a source of compressed air 27, and, installed on the removable portion 24, a nozzle 28 and a valve 29. The nozzle 28, shown in FIG. 4, comprises a venturi 30 and the removable portion 25 of the compressed air inlet 26 exits therein. The compressed air with a release of pressure in the venturi 30 acquires a supersonic speed able to carry out the suction of the liquid by the pipe 2. The valve 29 comprises an actuator 31 extending above the removable portion 24 and controlling a valve to open or close the removable portion 24 by the intermediary of a rod 33.

Figure 5:
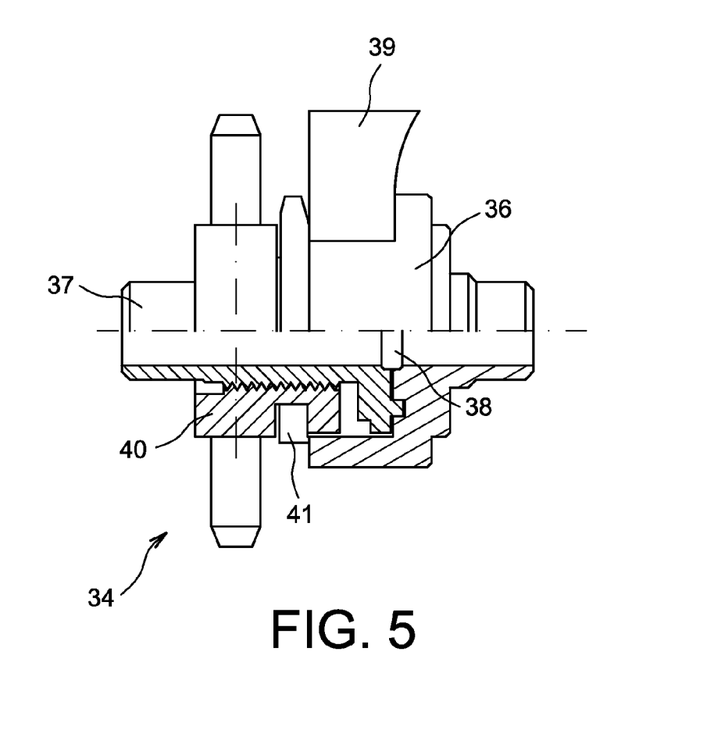

The suction unit 5 can be withdrawn from the rest of the device and then put back into place, being connected via three capstan connectors 34 to the compressed air inlet 26, to the connector 23 at the outlet of the selector 4 and to a third surface 35 of the pipe 2 after the valve 29 which leads to the outlet 6. The capstan connectors 34, shown more completely in FIG. 5, include a case 36 and an end 37 to be assembled together, the seal being formed by a double-cone seal 38 placed between them. The case 36 carried a container 39 in the shape of a trough receiving and maintaining the end of the tip 37. In addition, a capstan nut 40, engaged on an external threading of the tip 37, is also maintained by an external lip 41 of the container 39. A rotation applied to the capstan nut 40 displaces the tip 37 axially in the container 39 and compresses it against the case 36 by crushing the double-cone seal 38.

FIGS. 1 and 3 further show a discharge pipe 42 connecting the interior of the casing 19 to the outlet 6, and intended for the evacuation of the humidity in the selector 4.

When the compressed air is supplied, with the valve 29 open, the liquid is sucked from the chosen vat 1 toward the suction unit 5 and the outlet 6 fills the small reservoir 12 where it can be sampled. Note that the air inlet exits perpendicularly in the venturi 30, but the proper direction of air circulation is guaranteed by selecting the surfaces 14, 15 and 35 of the pipe 2 with diameters which become successively wider from the vat 1 to the outlet 6 (without considering the diameters at the nozzle 28), which can also be in a vacuum in relation to the vat 1: the resistance to the flow of the compressed air is therefore less substantial toward the outlet 6. But when the suction stops, the closing of the valve 29 has for effect to close the removable portion 24 and to inverse the direction of the flow of the compressed air toward the vat 1, by feeding back therein the liquid which may have stagnated in the device and in particular in the small reservoir 12 and the pipe 2. No other manoeuvre is required.

All of these movements are easy to accomplish through ordinary remote manipulators, with limited dexterity.

The invention claimed is:

1. A device for collecting liquid samples, comprising:
   a vat for containing a liquid;
   an outlet;
   a piping system connecting to a respective the vat to the outlet separate from the vat, the vat and the outlet being at opposite ends of the piping system;
   a compressed air inlet;
   a source of compressed air connected to the compressed air inlet; and
   a suction unit configured to suck the liquid from the vat, the suction unit comprising:
   a nozzle arranged in the piping system,
   a portion of the compressed air inlet that exits directly into the nozzle,
   a jug holder connected to the piping system and configured to receive a jug and transfer a sample of the liquid into the jug when the liquid is sucked from the vat, and
   a valve for selectively sealing off the pipe piping system, wherein the valve is arranged in the piping system between the nozzle and the outlet.

2. The device according to claim 1, wherein a first pipe section of the piping system arranged between the nozzle and the outlet has a wider cross-section than a second pipe section of the piping system arranged between the nozzle and the vat.

3. The device according to claim 1, wherein a pipe portion of the piping system, the portion of the compressed air inlet, the nozzle, and the valve form a unitary, removable part of the device, wherein the pipe portion of the piping system and the portion of the compressed air inlet respectively are removably connected to an adjacent pipe portion of the piping system and an adjacent portion of the compressed air inlet via connectors.

4. The device according to claim 3, wherein the connectors are capstan connectors.

5. The device according to claim 1, further comprising a quick coupling, wherein the jug holder comprises a first portion of the quick coupling and the piping system comprises a second portion of the quick coupling that is selectively connected to the first portion, said second portion being self-sealing and said first portion comprising a needle for sucking the sample of the liquid that is configured to penetrate through the second portion when the first and second portions are connected.

6. The device according to claim 5, wherein the piping system comprises a reservoir portion that is connected to the first portion of the quick coupling and the jug holder comprises a jug valve configured to selectively permit the sample of the liquid to be sucked via the needle.

7. The device according to claim 1, wherein the piping system is configured such that when the valve seals off the piping system, compressed air exiting into the nozzle is directed through the piping system in a first direction towards the end of the piping system where the vat is located, further wherein the piping system is configured such that when the valve does not seal off the piping system, compressed air exiting into the nozzle is directed through the piping system in a second direction that is inverse the first direction and towards the end of the piping system where the outlet is located.

8. The device according to claim 1, wherein the piping system is configured such that when the valve does not seal off the piping system, compressed air exiting into the nozzle causes a portion of the liquid to travel through the piping system from the vat to the outlet along a liquid path wherein the nozzle is downstream of a portion of the piping system where the jug holder connects.

9. A device for collecting liquid samples comprising:
   a plurality of vats containing liquids;
   an outlet;
   a piping system selectively connecting each of the vats to the outlet that is separate from the vats, the piping system comprising:
      a selector,
      a plurality of end portions, wherein the outlet and each of the vats are provided at a separate one of the end portions,
      a plurality of first pipe portions, wherein each first pipe portion provides fluid communication between the selector and a separate one of the vats, and
      a second pipe portion in fluid communication with the selector, wherein the selector is configured to selectively provide fluid communication between the second pipe portion and each of the first pipe portions; and
      a compressed air inlet;
   a source of compressed air connected to the compressed air inlet;
   a suction unit configured to suck the liquids from the vats, the suction unit comprising:
      a nozzle arranged in the piping system,
      a portion of the compressed air inlet that exits directly into the nozzle,
      a jug holder connected to the piping system and configured to receive a jug and transfer a sample of liquid into the jug when the liquid is sucked from one of the vats, and
      a valve for selectively sealing off the piping system, wherein the valve is arranged in the piping system between the nozzle and the outlet.

\* \* \* \* \*

UNITED STATES PATENT AND TRADEMARK OFFICE
CERTIFICATE OF CORRECTION

PATENT NO. : 8,758,708 B2
APPLICATION NO. : 13/497647
DATED : June 24, 2014
INVENTOR(S) : Brenneis et al.

It is certified that error appears in the above-identified patent and that said Letters Patent is hereby corrected as shown below:

In the Specification

Column 3, line 38, please insert -- 32 -- between "valve" and "to"

Signed and Sealed this
Eighteenth Day of November, 2014

Michelle K. Lee
*Deputy Director of the United States Patent and Trademark Office*

UNITED STATES PATENT AND TRADEMARK OFFICE
CERTIFICATE OF CORRECTION

Page 1 of 1

PATENT NO. : 8,758,708 B2
APPLICATION NO. : 13/497647
DATED : June 24, 2014
INVENTOR(S) : Brenneis et al.

It is certified that error appears in the above-identified patent and that said Letters Patent is hereby corrected as shown below:

On the title page item (73) replace "aux Enegies Alternatives, Paris (FR)" with --aux Energies Alternatives, Paris (FR)--

Signed and Sealed this
Twenty-sixth Day of January, 2016

Michelle K. Lee
*Director of the United States Patent and Trademark Office*